(12) United States Patent
Batista et al.

(10) Patent No.: US 12,053,027 B2
(45) Date of Patent: Aug. 6, 2024

(54) AEROSOL-GENERATING SYSTEM WITH CHROMATIC RECOGNITION

(71) Applicant: PHILIP MORRIS PRODUCTS S.A., Neuchâtel (CH)

(72) Inventors: Rui Nuno Batista, Morges (CH); Ricardo Cali, Mannheim (DE); Nikita Karelin, Moscow (RU)

(73) Assignee: Philip Morris Products, S.A., Neuchâtel (CH)

( * ) Notice: Subject to any disclaimer, the term of this patent is extended or adjusted under 35 U.S.C. 154(b) by 348 days.

(21) Appl. No.: 17/440,038

(22) PCT Filed: Mar. 13, 2020

(86) PCT No.: PCT/IB2020/052317
§ 371 (c)(1),
(2) Date: Sep. 16, 2021

(87) PCT Pub. No.: WO2020/194112
PCT Pub. Date: Oct. 1, 2020

(65) Prior Publication Data
US 2022/0175044 A1    Jun. 9, 2022

(30) Foreign Application Priority Data

Mar. 28, 2019   (EP) .................................... 19165976

(51) Int. Cl.
*A24F 40/51*    (2020.01)
*A24D 1/20*    (2020.01)
(Continued)

(52) U.S. Cl.
CPC ................ *A24F 40/51* (2020.01); *A24D 1/20* (2020.01); *A24F 40/70* (2020.01); *A24F 40/95* (2020.01); *G01N 21/255* (2013.01); *H02J 7/0044* (2013.01)

(58) Field of Classification Search
CPC .......... A24F 40/20; A24F 40/51; A24F 40/70; A61M 2205/3553; A61M 2205/3569;
(Continued)

(56) References Cited

U.S. PATENT DOCUMENTS 9,864,947 B1   1/2018  Sur et al.
10,362,804 B2  7/2019  Bessant et al.
(Continued)

FOREIGN PATENT DOCUMENTS

EP       2201850       6/2010
JP    2017501682 A     1/2017
(Continued)

OTHER PUBLICATIONS

International Preliminary Report on Patentability issued by the European Patent Office for PCT/IB2020/052317; Apr. 20, 2021: 10 pgs.
(Continued)

*Primary Examiner* — Jean F Duverne
(74) *Attorney, Agent, or Firm* — Mueting Raasch Group (57) ABSTRACT

An aerosol-generating system (50) has an optical sensor (23) disposed on a portion of an exterior surface of the aerosol-generating system. The optical sensor is configured to output sensor data. A controller (29) is operably coupled to the optical sensor. The controller is configured to manipulate one or more operating parameters of an aerosolizer element of the aerosol-generating system based on the optical sensor data.

18 Claims, 3 Drawing Sheets

(51) Int. Cl.
*A24F 40/70* (2020.01)
*A24F 40/95* (2020.01)
*G01N 21/25* (2006.01)
*H02J 7/00* (2006.01)

(58) Field of Classification Search
CPC .. A61M 2205/3584; A61M 2205/3592; A61M 2205/505; A61M 2205/6018; A61M 11/042; A61M 15/0035; A61M 2205/355306; A24D 1/20; G01N 21/255
See application file for complete search history.

(56) References Cited

U.S. PATENT DOCUMENTS

| | | | |
|---|---|---|---|
| 10,398,175 | B2 | 9/2019 | Thorens |
| 10,555,555 | B2 | 2/2020 | Fernando et al. |
| 10,575,562 | B2 | 3/2020 | Bless et al. |
| 11,033,054 | B2 | 6/2021 | Lamb et al. |
| 2005/0179893 | A1* | 8/2005 | Hill .................. G01N 21/6428 356/338 |
| 2016/0302488 | A1 | 10/2016 | Fernando |
| 2017/0020191 | A1 | 1/2017 | Lamb et al. |
| 2017/0196269 | A1 | 7/2017 | Bernauer et al. |
| 2017/0318861 | A1 | 11/2017 | Thorens |
| 2018/0104214 | A1 | 4/2018 | Raichman |
| 2019/0000144 | A1 | 1/2019 | Bless et al. |
| 2019/0086264 | A1 | 3/2019 | Morikawa et al. |
| 2020/0113239 | A1* | 4/2020 | Aller ................ A61M 15/0021 |

FOREIGN PATENT DOCUMENTS

| | | | |
|---|---|---|---|
| WO | 2015/022035 | 11/2015 | |
| WO | WO 2016/093043 A | 9/2017 | |
| WO | WO 2018/229102 A | 9/2017 | |
| WO | 2017/207442 | 12/2017 | |
| WO | 2019/049028 | 3/2019 | |
| WO | 2019/049029 | 3/2019 | |
| WO | WO-2019115464 A1 * | 6/2019 | ............... A24D 3/17 |
| WO | WO-2019121386 A1 * | 6/2019 | ............ A61M 15/00 |

OTHER PUBLICATIONS

International Search Report and Written Opinion for PCT/IB2020/052317 issued by the European Patent Office; Jun. 4, 2020: 11 pgs.
Written Opinion of the International Preliminary Examining Authority for PCT/IB2020/052317; Feb. 11, 2021: 6 pgs.
Extended EP Search Report for 19165976.2 issued by the European Patent Office; Oct. 28, 2019; 9 pgs.
Japanese Office Action for JP 2021-557543 issued by the Japanese Patent office on May 21, 2024; 8 pgs. including English machine translation.

* cited by examiner

AEROSOL-GENERATING SYSTEM WITH CHROMATIC RECOGNITION

This application is the § 371 U.S. National Stage of International Application No. PCT/IB2020/052317, filed 13 Mar. 2020, which claims the benefit of European Application No. 19165976.2, filed 28 Mar. 2019, the disclosures of which are incorporated by reference herein in their entireties.

The present disclosure relates to systems, devices, kits, and methods for use in chromatic recognition of aerosol-generating articles, and more specifically, to an optical sensor, such as a chromatic sensor, on an element of an aerosol-generating system. The optical sensor provides data to manipulate or modify one or more operating parameters of an element of the aerosol-generating system.

There is increasing demand for handheld aerosol-generating systems or devices that are able to deliver aerosol for user inhalation. Some aerosol-generating devices operate by heating an aerosol-forming substrate with a heating element. In particular, some devices operate by inserting an electrical heater into a solid aerosol-forming substrate and supplying power to the heater from a battery included in the device. Aerosol-generating devices may generate aerosol from an aerosol-generating substrate in response to a user action, such as a puff. Users typically hold aerosol-generating devices while puffing and in between puffs.

Known handheld electrically operated aerosol-generating systems typically comprise an aerosol-generating device or a main unit comprising a battery, control electronics and an electric heater for heating an aerosol-generating article designed specifically for use with the aerosol-generating device. In some examples, the aerosol-generating article comprises an aerosol-generating substrate, such as a tobacco rod or a tobacco plug. Aerosol-generating substrates, such as tobacco, typically comprise one or more volatile compounds that form an aerosol when heated inside the aerosol-generating device. The heater contained within the aerosol-generating device is inserted into or around the aerosol-generating substrate when the aerosol-generating article is inserted into the aerosol-generating device. In some electrically operated aerosol-generating systems, the aerosol-generating article may comprise a capsule containing an aerosol-generating substrate, such as loose tobacco.

Known handheld electrically operated aerosol-generating systems typically comprise an aerosol-generating device and a charging unit. The charging unit is configured to charge the aerosol-generating device and may be configured to house, contain, or store the aerosol-generating device between uses.

It would be desirable to provide users a convenient way to interact with their aerosol-generating system via color recognition, appearance or design. It would be desirable to provide users that wish to customize their aerosol-generating system a way to utilize color and modify the operation of the aerosol-generating system. It would be desirable to provide users a convenient way to modify the operation of the aerosol-generating system based on the color of the packaging for the consumable articles, the aerosol-generating system may be able to distinguish between consumable articles or aerosol-generating articles. It would be desirable to provide users a kit to allow users to personalize the appearance of their aerosol-generating system.

Various aspects of this disclosure relate to an aerosol-generating system having chromatic recognition. This disclosure provides systems, devices, kits, and methods for use in chromatic recognition of aerosol-generating articles, and more specifically, to an optical sensor, such as a chromatic sensor, on an element of an aerosol-generating system. The optical sensor provides data to manipulate one or more operating parameters of an element of the aerosol-generating system.

In one aspect of the disclosure, the aerosol-generating system comprises an optical sensor disposed on a portion of an exterior surface of the aerosol-generating system. The optical sensor is configured to output sensor data. A controller is operably coupled to the optical sensor. The controller is configured to manipulate one or more operating parameters of an aerosolizer element of the aerosol-generating system based on the optical sensor data.

The aerosol-generating system comprises an aerosol-generating device and a charging unit configured to charge and house the aerosol-generating device between uses. The optical sensor may be disposed on the exterior surface of the charging unit.

In an aspect of the disclosure, an aerosol-generating kit comprises the aerosol-generating system herein and two or more coloring elements configured to apply a color layer to the exterior surface of the aerosol-generating system.

The aerosol-generating kit may comprise the aerosol-generating system herein and packaging for containing aerosol-generating consumer articles. The packaging having a specific color associated with the aerosol-generating consumer articles.

The aerosol-generating kit may comprise the aerosol-generating system herein and a skin layer configured to be disposed onto the optical sensor. The skin layer having a specific color or configured to be colored.

The systems, devices, and methods may provide a cost effective and simple way that users can customize their aerosol-generating system in both appearance and operation. The optical sensor on the outer housing provides for orientation-free identification and avoids possible contamination from the consumable article or aerosol-generating article.

All scientific and technical terms used herein have meanings commonly used in the art unless otherwise specified. The definitions provided herein are to facilitate understanding of certain terms used frequently herein.

The term "aerosol-generating article" or "aerosol-generating substrate" refers to a substrate capable of releasing, upon heating, volatile compounds, which can form an aerosol. The aerosols generated from aerosol-generating substrates of smoking articles according to the present disclosure may be visible or invisible and may include vapours (for example, fine particles of substances, which are in a gaseous state, that are ordinarily liquid or solid at room temperature) as well as gases and liquid droplets of condensed vapours.

The term "controller" and "processor" refers to any device or apparatus capable of providing suitable computing capabilities and control capabilities such as, e.g., microprocessors, digital signal processors (DSP), application specific integrated circuits (ASIC), field-programmable gate arrays (FPGA), equivalent discrete or integrated logic circuitry, or any combination thereof and of providing suitable data storage capabilities that includes any medium (e.g., volatile or non-volatile memory, a CD-ROM, magnetic recordable medium such as a disk or tape, etc.) containing digital bits (e.g., encoded in binary, trinary, etc.) that may be readable and/or writeable.

The term "communication interface" refers to any device or apparatus capable of providing suitable data communication capabilities between an aerosol-generating device and a user interface device such as, e.g., various telemetry circuits and antennas and may use one or more wired or wireless (e.g., radio frequency) data transmission protocols such as, e.g., BLUETOOTH, WI-FI, any protocol in the ultra-high frequency (UHF) band, any protocol in the super high frequency (SHF) band, low frequencies, or combinations thereof.

The term "aerosol-generating device" refers to a device configured to use an aerosol-generating article or substrate to generate aerosol. In some embodiments, the aerosol-generating device may be described as a smoking article or a holder, particularly a tobacco stick holder. Preferably, the aerosol-generating device also includes an aerosolizer. The aerosolizer may include an atomizer, cartomizer, heater, or other aerosolizing components.

The term "aerosol-generating article or substrate" refers to a device or substrate that releases compounds that may form an aerosol to be inhaled by a user. In some cases, the substrate may release volatile compounds upon heating. Preferably, the aerosol-generating substrate includes nicotine. Suitable aerosol-forming substrates may include plant-based material. For example, the aerosol-generating substrate may include tobacco or a tobacco-containing material containing volatile tobacco flavor compounds, which are released from the aerosol-generating substrate upon heating. In addition, or alternatively, an aerosol-generating substrate may include a non-tobacco containing material. The aerosol-generating substrate may include homogenized plant-based material. The aerosol-generating substrate may include at least one aerosol former. The aerosol-generating substrate may include other additives and ingredients such as flavorants. In some embodiments, the aerosol-generating substrate is a liquid at room temperature. For example, the aerosol-generating substrate may be a liquid solution, suspension, dispersion or the like. A liquid aerosol-generating substrate may include glycerol, propylene glycol, water, nicotine and, optionally, one or more flavorants. In some embodiments, the aerosol-generating substrate is a solid at room temperature, such as a tobacco stick or nicotine powder.

The term "tobacco material" refers to a material or substance including tobacco, which includes tobacco blends or flavored tobacco, for example.

Having defined certain frequently-used terms above, aerosol-generating systems of the present disclosure will be described herein in more detail. In general, the aerosol-generating systems each include an optical sensor configured to detect chromatic information. The detected chromatic data may be used to modify an aerosol delivery profile or may be used in other ways that interest the user.

The aerosol-generating system may include one or more housings configured to be held by a user. In some embodiments, the system may include an aerosol-generating device having a housing. The system may include a charging unit having a separate housing. The housing of the aerosol-generating device may be configured to couple to the housing of the charging unit, for example, to be received by the charging unit. The charging unit may enclose the aerosol-generating device.

The aerosol-generating system includes an aerosol-generating device and a charging unit configured to charge and house the aerosol-generating device between uses. Preferably the optical sensor is disposed on the exterior surface of the charging unit.

The aerosol-generating device may include a battery. When operatively coupled together, the charging unit may recharge the aerosol-generating device. The charging unit may include a battery having a greater capacity than the battery of the aerosol-generating device.

The aerosol-generating device includes an aerosolizer. The aerosolizer is contained by the housing when used. The aerosolizer is configured to generate aerosol from an aerosol-generating substrate.

Any suitable type of aerosolizer may be used. In some cases, the aerosolizer may be thermally or fluidly coupled to the aerosol-forming substrate. The aerosolizer may be compatible for use with various types of aerosol-generating substrates.

The aerosolizer may include a heating blade for use with a solid aerosol-generating substrate. The heating blade may be coupled to the housing of the aerosol-generating device to receive electrical power from a power source (battery). For example, the aerosol-generating substrate may be provided in the form of a heat stick. The heating blade may be inserted into the heat stick and heated to generate aerosol from the solid substrate. The solid substrate may be a smoking material, such as tobacco. The heat provided by the heating blade to the heat stick may not burn the smoking material.

The aerosolizer may include a heater, a heater coil, a chemical heat source (such as a carbon heat source), or any suitable means that heats the substrate to generate aerosol. The aerosolizer may be coupled to the housing of the aerosol-generating device to receive electrical power from a power source (battery) and may be disposed adjacent to the substrate. For example, a heating element of a heater may be disposed adjacent to the aerosol-generating substrate and heated to generate aerosol from a liquid or solid substrate. A heater coil may include a susceptor adjacent to the aerosol-forming substrate and when an energized inductive coil is disposed adjacent to the susceptor, electromagnetic energy may be transferred to the susceptor to heat the substrate.

The aerosolizer may include an atomizer. A liquid aerosol-generating substrate may be contained in the substrate housing and in fluid communication with the atomizer. The atomizer may mechanically generate aerosol from the liquid substrate instead of relying only on temperature.

The aerosolizer may be compatible for use with an aerosol-generating substrate having a nicotine source and a lactic acid source. The nicotine source may include a sorption element, such as a PTFE wick with nicotine adsorbed thereon, which may be inserted into a chamber forming a first compartment. The lactic acid source may include a sorption element, such as a PTFE wick, with lactic acid adsorbed thereon, which may be inserted into a chamber forming a second compartment. The aerosolizer may include a heater to heat both the nicotine source and the lactic acid source. Then, the nicotine vapor may react with the lactic acid vapor in the gas phase to form an aerosol.

The aerosol-generating substrate is at least partially disposed in the aerosol-generating device when used. The aerosol-generating substrate may be removable after being consumed. A new aerosol-generating substrate may be received by the aerosol-generating device to replace the consumed substrate.

The aerosol-generating system includes one or more optical sensors configured to detect chromatic information. The optical sensor may be placed on an exterior surface of an element of the aerosol-generating system. Preferably the optical sensor may be placed on an exterior surface of the charging unit of the aerosol-generating system.

The aerosol-generating system includes a controller operably coupled to the optical sensor. The controller is configured to manipulate one or more operating parameters of an aerosolizer element of the aerosol-generating system based on the optical sensor data. The controller may be configured to automatically modify one or more operating parameters of an aerosolizer element of the aerosol-generating system based on the optical sensor data.

The optical sensor may be a chromatic sensor configured to detect chromatic information. Chromatic information refers to colour information. The optical sensor may be configured to sense and output sensor data that corresponds to a colour detected by the optical sensor. The output sensor data may be utilized by the controller to manipulate or modify the operation of an aerosolizer element of the aerosol-generating system or the aerosol-generating device based on the output sensor data. For example, the output sensor data may increase or decrease the temperature rise or change in temperature or temperature profile of the aerosolizer element of the aerosol-generating system or the aerosol-generating device based on the output sensor data.

In some embodiments, a user may place an aerosol-generating substrate or article in optical communication with the optical sensor. The optical sensor may detect the colour of the aerosol-generating substrate or article (or its packaging) to modify the operation of the aerosolizer element of the aerosol-generating system or the aerosol-generating device based on the output sensor data. In this manner, operation of the aerosolizer element of the aerosol-generating system or the aerosol-generating device may have a number of pre-set operation parameters that are utilized for specific aerosol-generating substrate or article, based on the colour of the aerosol-generating substrate or article or the colour of the packaging of the aerosol-generating substrate or article.

The optical sensor may be optically coupled to packaging for aerosol-generating articles and the controller is configured to manipulate one or more operating parameters of an aerosolizer element of the aerosol-generating system based on the color of the packaging that is detected by the optical sensor.

In some embodiments the user may apply a color layer to the optical sensor. The color layer may be applied via coloring elements. Coloring elements may include color markers or pens. The color layer may be applied via a skin layer or mask layer, or stencil layer. The user may thus customize the housing of the aerosol-generating system, or charging unit utilizing color.

The user applied color may be optically coupled to the optical sensor and the optical sensor may detect the applied colour to modify the operation of the aerosolizer element of the aerosol-generating system or the aerosol-generating device based on the output sensor data. In this manner, operation of the aerosolizer element of the aerosol-generating system or the aerosol-generating device may have a number of pre-set operation parameters that are utilized as directed by the user by the application of specific colors to the optical sensor.

The optical sensor may be a board on chip type sensor. The optical sensor may be operably coupled to an electronics control unit or controller. The controller may include memory storing one or more aerosol delivery profiles or aerosol forming heating profiles that are associated with the color or chromatic data generated by the optical sensor. The controller may be contained within the charging unit. The controller may be contained within the aerosol-generating device. Both the charging unit and the aerosol-generating device may include a controller.

The optical sensor may include a chromatic sensor and a light source, such as a solid state light source. The chromatic sensor may sense light from the light source that is reflected off of a colored surface proximate to the optical sensor. The optical sensor may include a light transparent layer forming a portion of the exterior surface of the aerosol-generating system.

The colored surface may be referred to as a "target" and may include any suitable colored surface, as described herein. The solid state light source of the optical sensor may provide uniform reproducible illumination of the target surface.

Once the reflected light reaches the optical sensor, the optical sensor may transmit a specific electronic signal accordingly, which is analysed by the electronic control unit or controller which then compares the matching with a defined related data. If such data matches a defined target an electronic signal than triggers action as programmed incorporated in the control unit. These triggered actions include one or more of, turning ON a set of LED lights incorporated in the device which can light in different colors, or changing the operating mode of the device, in terms of the temperature profile, the duration of the consumer experience (such as an aerosol delivery profile), or unlocking or locking the device for uses, or reset the device to original manufacturing pre-sets.

Therefore, as described above, this invention enables consumers to customize the covers of the device with given colors, enhance it based on retro-illumination given by LEDs existing incorporated in the cover(s), which lighting can be dynamic over time in terms of different colors and light intensity.

As well as approaching a given packaging with a specific color in at least one of its surfaces, close to the sensor existing in the device, such color will be recognized by the device as one of the pre-set colors, as programmed, and therefore acting accordingly changing the operating mode of the device for that specific consumable, based on the color of its packaging.

One advantage is when the colors of the packaging of the consumables are not recognized by the programming of the device means that it's a competitors products or a counterfeit product, and therefore the device will not operate.

Specific coloring processes may create and define a specific pigmentation in the surface of product packaging (target), including metallic particles which give specific light reflections, and which will generate unique color patterns, and therefore also unique in terms of its reproducibility, difficult to copy.

In one embodiment, an aerosol-generating kit includes the aerosol-generating system described herein and two or more coloring elements configured to apply a color layer to the exterior surface of the aerosol-generating system.

In one embodiment, an aerosol-generating kit includes the aerosol-generating system described herein and packaging for containing aerosol-generating consumer articles. The packaging has a specific color associated with the aerosol-generating consumer articles.

In one embodiment, an aerosol-generating kit includes the aerosol-generating system described herein and a skin layer configured to be disposed onto the optical sensor. The skin layer has a specific color or configured to be colored.

The invention may provide orientation-free identification of the target color. The invention may provide a contamination-free method of sensing the target color. The invention may provide the consumer with a unique method of customizing the system while also changing or interacting with the operating parameters of the system via the use or identification of color.

The aerosol-generating device may include a controller. The controller may be operatively coupled to the aerosolizer.

The controller may also be operatively coupled to the optical sensor either directly or via the controller contained within the charging unit. The controller of the aerosol-generating device may be contained by the housing of the aerosol-generating device. The controller is configured to activate the aerosolizer to generate aerosol from the aerosol-forming substrate. The aerosolizer may be activated to generate aerosol according to an aerosol delivery profile.

The charging unit may include a controller separate from the controller of the aerosol-generating device. When the charging unit includes the optical sensor, the controller may also be operatively coupled to the optical sensor. The controller of the charging unit may be contained by the housing of the charging unit.

The functionality described herein with respect to the optical sensors may be carried out by one or more controllers, for example, in the aerosol-generating device or the charging unit. In particular, one or more of the controllers are configured to provide aerosol delivery profiles on the at least one color characteristic detected by the optical sensor when operatively connected to the optical sensor.

The aerosol delivery profiles (or other operational parameters of the device) determined from the detected color characteristics may be communicated between the aerosol-generating device and the charging unit. In one example, one or more of the controllers includes a communication interface configured to operatively communicate the color data. The communication interface of the aerosol-generating device, for example, may be configured to communicate color data to at least one of the charging unit and a separate user interface. The separate user interface may be part of a device separate from the aerosol-generating system, such as a smartphone, tablet, or wearable device of the user (for example, a smartwatch). The separate user interface may include a display or a speaker to relay information to the user, for example using graphics or audio. The color data may also be used as an input to one or more applications running on the separate user interface.

The separate user interface may be an Internet-enabled device. Color data may be communicated to the Internet-enabled device, which may communicate the color data over the Internet for remote storage or use. For example, color data may be stored on a remote server. The remote server may be used to further process the data or store it for later access, for example, by the user on a cloud-based data interface.

The communication interface may be any suitable interface, wired or wireless, configured to communicate data between devices, such as universal serial bus (USB), powerline, Wi-Fi, Bluetooth, and cellular data networks.

Various devices may be connected to the communication interface or removed over time. The communication interface may be configured to receive data from other devices. Such received data may be provided to the user, for example, using a user interface of the aerosol-generating system.

The aerosol-generating system may also include one or more user interfaces to provide color data to the user. In some embodiments, a display or a speaker is operatively coupled to one or more of the controllers. The display may be configured, for example, to display graphics based on the color data. Graphics may include alphanumerical characters or other images.

One or more controllers may include memory. The memory may be used to store various types of data, such as the color data. Stored color data may be later used, displayed, or communicated. In one example, color data may be determined and stored on the controller of the aerosol-generating device. In another example, color data may be determined and stored on the controller of the charging unit. In further examples, color data may be communicated from the aerosol-generating device to the charging unit and stored, or vice versa.

Color data may be used by the controller to modify the aerosol delivery profile. The aerosol delivery profile describes how the aerosol is generated from the aerosol-forming substrate and delivered to the user. For example, the aerosol delivery profile may adjust the activation of the aerosolizer to increase or reduce the amount of aerosol being generated. In some embodiments, the aerosol delivery profile includes a nicotine delivery profile. The nicotine delivery profile may describe how much nicotine is being delivered to the user.

The aerosol delivery profile may be selected from a plurality of pre-programmed aerosol delivery profiles. The pre-programmed aerosol delivery profiles may be stored on the memory of the controller or communicated to the controller, for example, from another controller or user device (for example, a smartphone). Each aerosol delivery profile may be appropriate for different color data sensed by the optical sensor.

The controller may be provided in any suitable form and may, for example, include a processor and a memory. Generally, the controller includes memory that contains instructions that cause one or more components to carry out a function or aspect of the controller. Functions attributable to controller in this disclosure may be embodied as one or more of software, firmware, and hardware.

In particular, one or more of the components, such as controllers, described herein may include a processor, such as a central processing unit (CPU), computer, logic array, or other device capable of directing data coming into or out of the controller. The controller may include one or more computing devices having memory, processing, and communication hardware. The controller may include circuitry used to couple various components of the controller together or with other components operably coupled to the controller. The functions of the controller may be performed by hardware and/or as computer instructions on a non-transient computer readable storage medium.

The processor of the controller may include any one or more of a microprocessor, a microcontroller, a digital signal processor (DSP), an application specific integrated circuit (ASIC), a field-programmable gate array (FPGA), and/or equivalent discrete or integrated logic circuitry. In some examples, the processor may include multiple components, such as any combination of one or more microprocessors, one or more controllers, one or more DSPs, one or more ASICs, and/or one or more FPGAs, as well as other discrete or integrated logic circuitry. The functions attributed to the controller or processor herein may be embodied as software, firmware, hardware, or any combination thereof. While described herein as a processor-based system, an alternative controller could utilize other components such as relays and timers to achieve the desired results, either alone or in combination with a microprocessor-based system.

In one or more embodiments, the exemplary systems, methods, and interfaces may be implemented using one or more computer programs using a computing apparatus, which may include one or more processors and/or memory. Program code and/or logic described herein may be applied to input data/information to perform functionality described herein and generate desired output data/information. The output data/information may be applied as an input to one or more other devices and/or methods as described herein or as would be applied in a known fashion. In view of the above, it will be readily apparent that the controller functionality as described herein may be implemented in any manner known to one skilled in the art.

The controller may be configured to regulate a supply of power. For example, the power supplied to the aerosolizer may be managed by the controller, for example, to regulate the generation of aerosol from the aerosol-forming substrate.

Figure 1A:
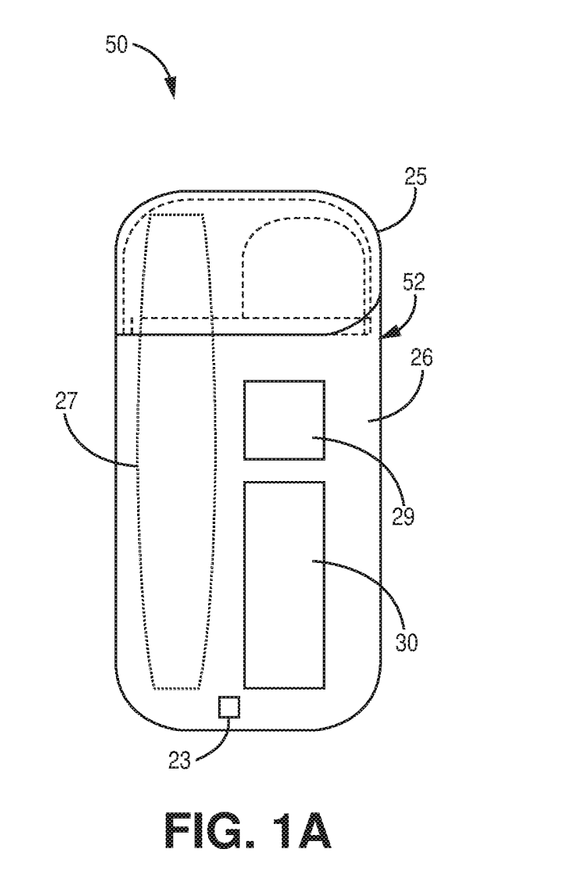
FIGS. 1A-B are schematic illustrations showing an example of one charging unit of the aerosol-generating system in a closed position and an open position, respectively.
Figure 1B:
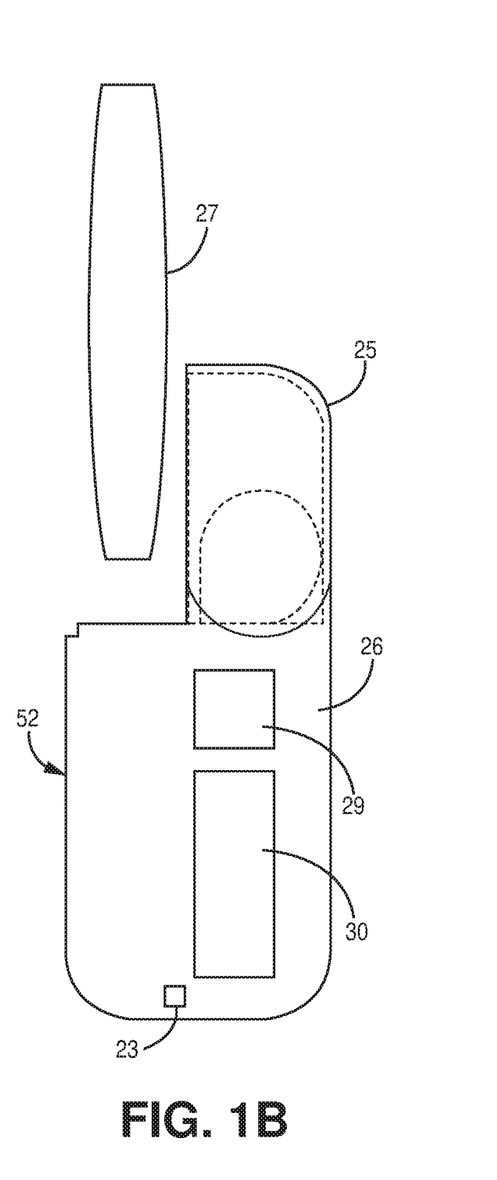
Figure 2:
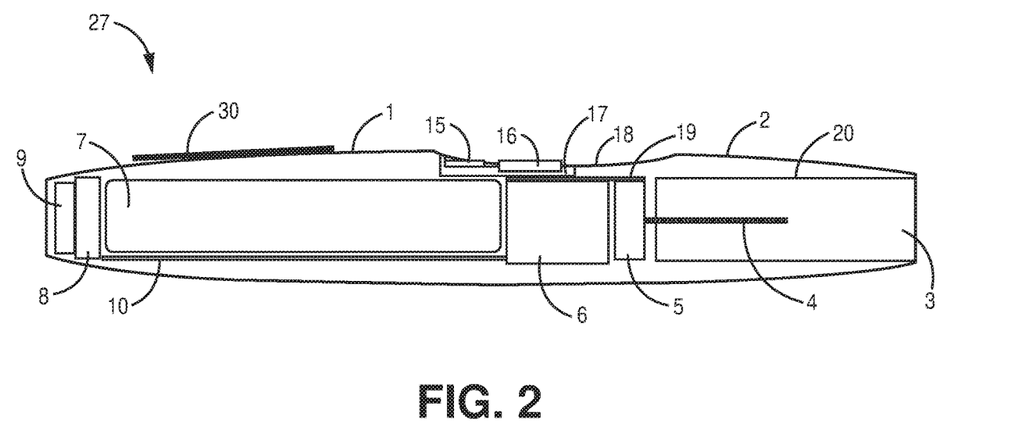
FIG. 2 is a schematic illustration showing an example of one aerosol-generating device of the aerosol-generating system in a cross-section view.

FIGS. 1A-B show aerosol-generating system 50 including a charging unit 52, which includes a cover 25 (lid) and main charging unit 26 (body). Cover 25 may be opened (FIG. 2A) or closed (FIG. 2B). Cover 25 opens smoothly at least up to about 90 degrees to provide sufficient clearance for the user's finger. When cover 25 is opened, the user may remove the aerosol-generating device 27 from the main charging unit 26.

Aerosol-generating system 50 includes an optical sensor 23. The optical sensor 23 may be disposed on a portion of the exterior surface of the aerosol-generating system 50. The optical sensor 23 may be disposed on a portion of the exterior surface of the main charging unit 52. The optical sensor 23 may be disposed on a portion of the exterior surface of the main charging unit body 26.

Aerosol-generating system 50 includes a controller 29. The controller 29 is operably coupled to the optical sensor 23. The controller 29 is configured to manipulate one or more operating parameters of an aerosolizer element of the aerosol-generating system 50 based on the optical sensor data.

Cover 25 defines a cavity with sufficient inner volume to accommodate the aerosol-generating device 27. As shown in FIG. 2A, aerosol-generating device 27 may be inserted into charging unit 52. Cover 25 may be closed to contain and protect aerosol-generating device 27 when charging.

Main charging unit 26 includes electronic control unit 29 (controller) and power supply 30, which may include a battery or batteries. Power supply 30 is typically larger and contains more charge than the aerosol-generating device 27 power supply 7 (FIG. 2). Although not shown, charging unit 52 may include a communication interface, wired or wireless, that communicates with aerosol-generating device 27, for example using electrical unit 8 (FIG. 2).

FIG. 2 illustrates an aerosol-generating device 27 including main tobacco stick holder 1, or controller portion, and cover 2, or mouth portion. Main tobacco stick holder 1 and cover 2 together define the housing of aerosol-generating device 27. Cover 2 defines cavity 3, which is configured to receive a tobacco heat stick (not shown). The tobacco heat stick may be pierced by heating element 4 (aerosolizer) when inserted into cavity 3. Heating element 4 is provided in the form of a blade or pin, for example, and utilizes a resistor for resistive heating or a susceptor for induction heating.

Heating element 4 raises the temperature of the tobacco heat stick when activated. Holder 5, or base of heating element 4, provides electrical connectivity (operative coupling) between heating element 4 and electronic control unit 6 (controller). Electronic control unit 6 is operatively coupled to power supply 7, which may include a battery or batteries. Electronic control unit 6 is used to activate, or to deliver power to, the heating element. Electrical unit 8 (communication interface) with a printed circuit board is operatively coupled to electronic control unit 6 and power supply 7. Electrical unit 8 is operatively coupled to electrical or data contact pads 9, which may be used to couple to an external power supply for charging and an external device for communicating data. Connectivity substrate 10, or the wiring of a flat flexible substrate, may be used to operatively couple electrical unit 8 and electronic control unit 6.

Light-emitting diode 15 is provided along main tobacco stick holder 1 and provides status indications, such as on/off or an operating mode. Light-emitting diode 15 may be color coded to provide such indications. Operating button 16, or actuator, is provided along main tobacco stick holder 1 and allows the user to turn aerosol-generating device 1 on or off, as well as access certain menu modes. Light-emitting diode 15 and operating button 16 are operatively coupled to printed circuit board 17. Printed circuit board 17 is operatively coupled to electronic control unit 6 through connectivity substrate 19, or the wiring of a flat flexible substrate. Recessed surface 18 may be provided along main tobacco stick holder 1 to provide ergonomic contact with, and protection of, light-emitting diode 15 and operating button 16 for the user's fingers. In particular, recessed surface 18 provides some protection from unintended actuation of operating button 16. Main tobacco stick holder 1 may include display 30 (user interface), which may display alphanumeric graphics or other graphics visible to the user.

Cavity housing 20 defines cavity 3 and provides air management around the tobacco heat stick when inserted into cavity 3. Cavity housing 20 may also be used to extract the tobacco heat stick from the aerosol-generating device 1.

Figure 3:
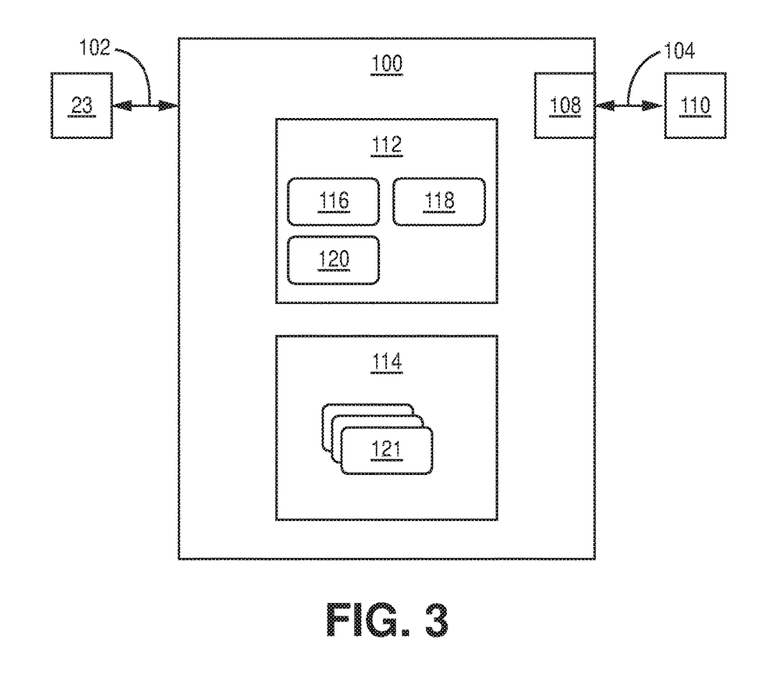
FIG. 3 is a schematic illustration of an example of one controller of the aerosol-generating system.

FIG. 3 shows controller 100 with operative coupling 102 to optical sensor 23 and operative coupling 104 to other device 110 using communication interface 108. Controller 100 may be contained in an aerosol-generating device or a charging unit. Other device 110 may be aerosol-generating device 27, charging unit 52, or an external Internet-enabled device separate from the aerosol-generating system.

Controller 100 includes processor 112 and memory 114. Processor 112 receives color or chromatic data 116 and determines operation data 118 based on color or chromatic data 116. Processor 112 determines aerosol delivery profile 120 based on color data 118 and optionally other input received using communication interface 108 or by a user interface (not shown). Memory 114 stores pre-programmed aerosol delivery profiles 121. Aerosol delivery profile 120 may be selected by processor 112 from pre-programmed aerosol delivery profiles 121.

Figure 4:
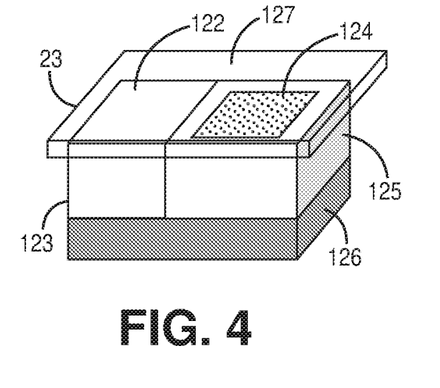
FIG. 4 is an illustration of an example of an optical sensor in perspective view.
Figure 5:
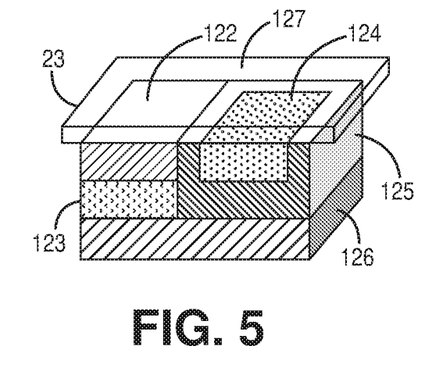
FIG. 5 is an illustration of an example of an optical sensor in cross-section perspective view.
Figure 6:
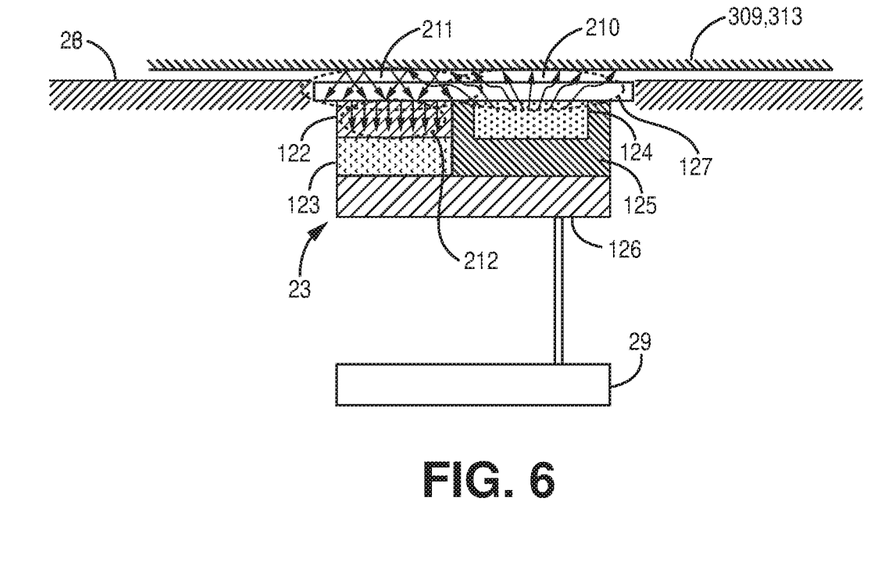
FIG. 6 is a schematic illustration of an example of an optical sensor forming a portion of the exterior surface of an element of the aerosol-generating system in a cross-section view.

FIG. 4 is an illustration of an example of an optical sensor 23 in perspective view. FIG. 5 is an illustration of an example of an optical sensor 23 in cross-section perspective view. FIG. 6 is a schematic illustration of an example of an optical sensor 23 forming a portion of the exterior surface 26 of an element of the aerosol-generating system in a cross-section view.

The optical sensor 23 or chromatic sensor 23 includes a light sensitive sensor 123 and a light source 124 on a substrate or chip 126. The substrate or chip 126 may be referred to as a board on-chip and may provide electronic circuitry to enable components (such as a controller 29) to interface and connect with the optical sensor 23 or light sensitive sensor 123.

The light sensitive sensor 123 and a light source 124 may be arranged side-by-side. Light source housing 125 may contain and direct light towards the target 309, 313. A polarizer element 122 may be disposed on the light sensitive sensor 123 to direct light in a parallel manner (unidirectional light 212) onto the light sensitive sensor 123.

Emitted light 210 from the light source 124 may transmit through a light transparent layer 127 and then reflect off of the target 309, 313. This reflected light 211 may be incident onto the optical sensor 23 or light sensitive sensor 123 via the light transparent layer 127 and the optional polarizer element 122.

The specific embodiments described above are intended to illustrate the invention. However, other embodiments may be made without departing from the scope of the invention as defined in the claims, and it is to be understood that the specific embodiments described above are not intended to be limiting.

As used herein, the singular forms "a," "an," and "the" encompass embodiments having plural referents, unless the content clearly dictates otherwise.

As used herein, "or" is generally employed in its sense including "and/or" unless the content clearly dictates otherwise. The term "and/or" means one or all the listed elements or a combination of any two or more of the listed elements.

As used herein, "have," "having," "include," "including," "comprise," "comprising" or the like are used in their open-ended sense, and generally mean "including, but not limited to". It will be understood that "consisting essentially of," "consisting of," and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

The invention claimed is:

1. An aerosol-generating system comprising:
an optical sensor disposed on a portion of an exterior surface of the aerosol-generating system, the optical sensor configured to output sensor data;
a controller operably coupled to the optical sensor, the controller is configured to manipulate one or more operating parameters of an aerosolizer element of the aerosol-generating system based on the optical sensor data,
wherein the optical sensor is configured to be optically coupled to packaging for aerosol-generating articles and the controller is configured to manipulate one or more operating parameters of an aerosolizer element of the aerosol-generating system based on the color of the packaging that is detected by the optical sensor; and
wherein aerosol-generating system comprises an aerosol-generating device and a charging unit configured to charge and house the aerosol-generating device between uses, and the optical sensor is disposed on the exterior surface of the charging unit.

2. The aerosol-generating system according to claim 1, wherein the optical sensor is a chromatic sensor.

3. The aerosol-generating system according to claim 1, wherein the controller is configured to automatically modify one or more operating parameters of an aerosolizer element of the aerosol-generating system based on the optical sensor data.

4. The aerosol-generating system according to claim 1, further comprising coloring elements configured to apply a color layer to the exterior surface of the aerosol-generating system.

5. The aerosol-generating system according to claim 1, wherein the optical sensor comprises a chromatic sensor and a light source, such as a solid state light source.

6. The aerosol-generating system according to claim 1, wherein the optical sensor comprises a light transparent layer forming a portion of the exterior surface of the aerosol-generating system.

7. An aerosol-generating kit comprising:
the aerosol-generating system according to claim 1; and
two or more coloring elements configured to apply a color layer to the exterior surface of the aerosol-generating system.

8. An aerosol-generating kit comprising:
the aerosol-generating system according to claim 1; and
packaging for containing aerosol-generating consumer articles, the packaging having a specific color associated with the aerosol-generating consumer articles.

9. An aerosol-generating kit comprising:
the aerosol-generating system according to claim 1; and
a skin layer configured to be disposed onto the optical sensor, the skin layer having a specific color or configured to be colored.

10. The aerosol-generating system according to claim 2, further comprising coloring elements configured to apply a color layer to the exterior surface of the aerosol-generating system.

11. The aerosol-generating system according to claim 3, wherein the optical sensor comprises a chromatic sensor and a light source, such as a solid state light source.

12. The aerosol-generating system according to claim 2, wherein the optical sensor comprises a light transparent layer forming a portion of the exterior surface of the aerosol-generating system.

13. The aerosol-generating system according to claim 3, wherein the optical sensor comprises a light transparent layer forming a portion of the exterior surface of the aerosol-generating system.

14. The aerosol-generating system according to claim 4, wherein the optical sensor comprises a chromatic sensor and a light source, such as a solid state light source.

15. The aerosol-generating system according to claim 4, wherein the optical sensor comprises a light transparent layer forming a portion of the exterior surface of the aerosol-generating system.

16. An aerosol-generating kit comprising:
the aerosol-generating system according to claim 2; and
two or more coloring elements configured to apply a color layer to the exterior surface of the aerosol-generating system.

17. An aerosol-generating kit comprising:
the aerosol-generating system according to claim 2; and
packaging for containing aerosol-generating consumer articles, the packaging having a specific color associated with the aerosol-generating consumer articles.

18. An aerosol-generating kit comprising:
the aerosol-generating system according to claim 2; and a skin layer configured to be disposed onto the optical sensor, the skin layer having a specific color or configured to be colored.

\* \* \* \* \*